US00PP18653P3

(12) United States Plant Patent
Psenner

(10) Patent No.: US PP18,653 P3
(45) Date of Patent: Mar. 25, 2008

(54) ***LANTANA* PLANT NAMED '2003.219'**

(50) Latin Name: *Lantana*
Varietal Denomination: 2003.219

(75) Inventor: Thomas Psenner, Eppan (IT)

(73) Assignee: Amerinova Properties, LLC, Bonsall, CA (US)

( * ) Notice: Subject to any disclaimer, the term of this patent is extended or adjusted under 35 U.S.C. 154(b) by 0 days.

(21) Appl. No.: 11/475,504

(22) Filed: Jun. 27, 2006

(65) Prior Publication Data

US 2007/0300337 P1 Dec. 27, 2007

(51) Int. Cl.
*A01H 5/00* (2006.01)

(52) U.S. Cl. ..... Plt./227

(58) Field of Classification Search ..... Plt./227
See application file for complete search history.

*Primary Examiner*—Kent Bell
*Assistant Examiner*—S. B. McCormick-Ewoldt

(57) ABSTRACT

A new and distinct cultivar of *Lantana* plant named 2003.219, characterized by its relatively large, 2" umbels, flower color which is salmon/orange at opening, maturing to a yellow/orange and then to a lavender purple, and by its moderate vigor with an upright habit and excellent branching.

1 Drawing Sheet

The present invention relates to a new and distinct cultivar of *Lantana* plant, botanically known as *Lantana camara,* and referred to by the varietal denomination '2003.219'.

The new cultivar is the product of a planned breeding program carried out by the inventor in Bozen, Italy. The female or seed parent was the proprietary cultivar *Lantana camara* 'Viola' (not patented), and the male or pollen parent was the proprietary cultivar *Lantana camara* 'Mini red' (not patented). The objective of the breeding program was to create *Lantana* cultivars having new colors, large flowers, and a compact growth habit.

The new cultivar was selected by the inventor from the progeny of the stated cross in a cultivated area in Bozen, Italy. The first act of asexual reproduction of the new cultivar was accomplished when vegetative cuttings were from the selection on May 3, 2003 in a controlled environment in Bozen, Italy, by or under the supervision of the inventor. Horticultural examination of controlled flowerings of successive plantings has shown that the unique combination of characteristics of the new cultivar are firmly fixed and are retained through successive generations of asexual reproduction.

The new cultivar has not been observed under all possible environmental conditions. The phenotype may vary significantly with variations in environment such as temperature, light intensity and day length without, however, any variance in genotype. The following observations, measurements and comparisons describe plants grown in Loudon, N.H. and Bonsall, Calif. under normal commercial growing conditions.

SUMMARY OF THE INVENTION

The following traits have been repeatedly observed and have been determined to be basic characteristics of the new cultivar, which in combination distinguish the new cultivar as being new and distinct:

1. The umbels of the new cultivar are very large, being 2 inches in diameter.

2. As the flower buds expand, the opening color is salmon-orange. When the flowers are fully open, the color is a bright yellow to yellow orange, and as the flowers age, the flower color changes first to salmon orange and then to lavender purple. Under brighter light and cooler temperatures, the flower color tends to intensify.
3. The new cultivar has moderate vigor, with an upright habit and excellent branching. Internode length ranges between 2" and 3".
4. The leaves are ovate in shape, and when fully expanded are 4-5" in length and 2-3" in width at the widest point.

The new cultivar differs from its male parent primarily by its upright growth habit, larger leaf size, and the lavender purple color of its fully mature and aging flowers. The new cultivar differs from its female parent primarily by its upright habit and its large flower size.

Of the many commercial cultivars known to the present inventor, the most similar in comparison to the new cultivar is the cultivar 'Anne Marie', disclosed in U.S. Plant Pat. No. 11,310. In comparisons made in Loudon, N.H., plants of the new cultivar were significantly more vigorous than plants of 'Anne Marie'. In addition, when the flowers of the new cultivar are expanding to a fully open condition, the yellow to yellow-orange flower color is distinctly different than the orange-red flower color of 'Anne Marie'.

BRIEF DESCRIPTION OF THE PHOTOGRAPHS

The photograph at the bottom of the single sheet comprises a front perspective view of a typical flowering plant of the new cultivar. The photograph at the top shows a series of fully open flowers of the new cultivar. The photographs show the colors of the new cultivar as true as is reasonably possible with colored reproductions of this type. If any differences exist between the photographic color and the color values described below, the values in the detailed description are accurate.

DETAILED BOTANICAL DESCRIPTION

In the following description color references are made to The Royal Horticultural Society Colour Chart. The values are based on plant material approximately 8-9 months old grown in Bonsall, Calif., and the values were taken in early May.

Botanical classification: *Lantana camara* cv '2003.219'.

*Seed parent.*—*Lantana camara* 'Viola'.

*Pollen parent.*—*Lantana camara* 'Mini red'.

Propagation:

*Type.*—Leaf cuttings.

*Rooting description.*—Fine, freely branching and fibrous.

Plant description:

*General appearance and form.*—Round, compact, nice mounding habit.

*Growth and branching habit.*—Free branching, laterals tend to grow out from center, foliage is very dense.

*Plant habit.*—Vigorous growth habit.

*Plant height.*—20 cm.

*Plant width.*—45 cm.

*Number of branches per plant.*—Four main stems, each with three secondary shoots.

*Length.*—Main stem about 22 cm, although highly variable.

*Width.*—0.4 cm.

*Internode length.*—About 3.5 cm.

*Color.*—Young stems are approximately 144A; bark at woody base is 199A.

Foliage description:

*Arrangement.*—Opposite; simple.

*Length.*—About 7.8 cm.

*Width.*—About 5.0 cm.

*Shape at apex.*—Acute to acuminate.

*Shape at base.*—Obtuse.

*Margin.*—Serrated.

*Color of young foliage.*—Upper surface: 137A. Lower surface: 137B.

*Color of mature foliage.*—Upper surface: 147A. Lower surface: Darker than 147B.

*Venation pattern.*—Arcuate to netted.

*Venation color.*—Upper surface 146A, lower surface 146B.

*Petiole length.*—About 1.8 cm.

*Petiole diameter.*—About 0.2 cm.

*Petiole color.*—Upper surface, 146A, lower surface 146B.

*Additional comments.*—Leaves are coarse and sandpapery. There are stiff hairs on top surface, with the bottom surface being only minutely pubescent. The leaves have a sharp herbaceous scent. The petioles are minutely pubescent.

Inflorescence description:

*Appearance.*—Solitary, axillary, round umbel-type inflorescences, two per node at shoot tips. Each inflorescence has about 26 florets which are tubular with flaring lobes that tend to curl upward. Florets are slightly asymmetric. Floret anthesis is acropetal. For umbels, development is outer toward the center.

*Quantity.*—Freely flowering; more than 20 open flowers and buds per plant, with about 6 umbels having florets open or in the opening process, and 14 umbels in bud.

*Buds.*—Rate of opening: 3 to 5 days for each floret, with florets opening sequentially from the outer umbel to the center; one umbel can take 7-12 days for all florets to open. Height: About 2.0 cm. Diameter: About 4.0 cm. Shape: Round, mounded, generally hemispherical. Floret buds: Color 168A, length 1.4 cm., width 0.4 cm.

*Flowers* (*individual florets within umbel*).—Depth: About 1.7 cm. Diameter: About 0.8-1.0 cm. Corolla: Petal length: 0.4 cm. Petal width: 0.5 cm. Number of petals: 4, fused into a slender corolla tube at base; tube is 1.2 cm long and 0.25 cm wide. Petal shape: Rounded, rectangular. Petal apex: Rounded. Petal margin: Entire, but sinuate. Texture: Smooth. Color, upper surface when opening: 7A lower surface when opening: 8C upper surface, opened flower: base color is 7A, margins when mature are tinted between 33A and 33B with the color upon further aging becoming lavender purple between 77B and 77C lower surface, opened flower: 8C. Corolla tube: 180C. Calyx Appearance: Short, small, fused into tiny cup. Sepal shape: No distinct sepals. Length: 0.3 cm. Diameter: 0.2 cm. Number of sepals: Indeterminate due to complete fusing. Color, inner surface 145B outer surface 145A. Peduncle (for umbel) Strength: Good. Angle: About 45 degrees from stem axis. Length: 2.4 cm. Color: 144B. Texture: Pubescent. Additional comments: florets are sessile, that is, without pedicels. Each floret within umbel is subtended by a tiny bract (0.2 cm by 0.5 cm and color 144A).

Reproductive organs:

*Stamen number.*—4 per floret, adnate to the corolla tube which is fused around style.

*Stamen length.*—About 0.3 cm.

*Anther shape.*—Oval.

*Anther length.*—Less than 0.1 cm.

*Anther color.*—160A.

*Pollen.*—Very scarce but 11c when present.

*Pistil length.*—About 0.4 cm.

*Stigma shape.*—Round.

*Stigma color.*—145A.

*Style length.*—About 0.2 cm.

*Style color.*—145D.

*Ovary color.*—145B.

Seed: No seed has been observed.

Disease/pest susceptibility: No particular susceptibility has been noted.

Temperature tolerance: Flowering will stop at temperatures below 40 deg. Flowering will continue at temperatures as high as 98 deg. F. in Loudon, N.H.

Growth retardants: No growth retardants necessary.

Fragrance: Umbels have no fragrance.

I claim:

1. A new and distinct cultivar of *Lantana* plant named 2003.219, as illustrated and described.

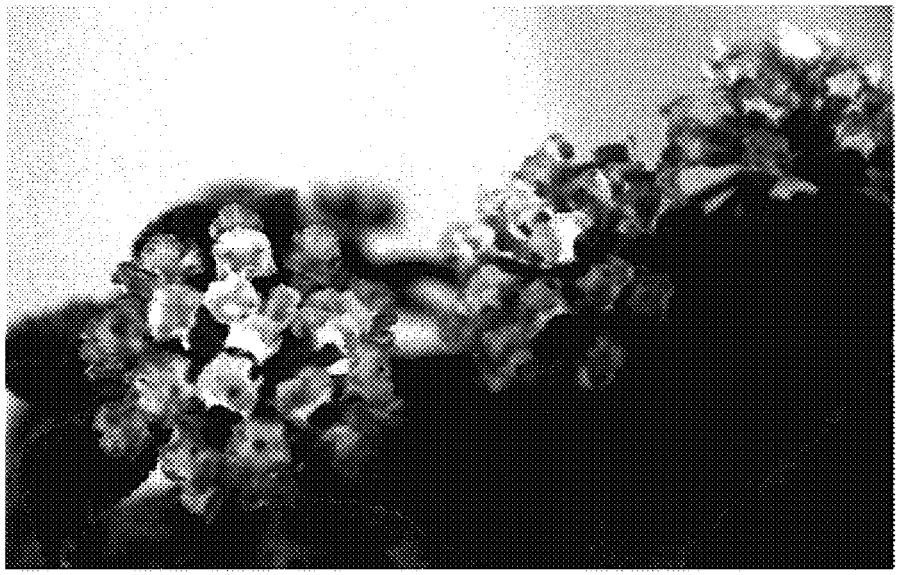
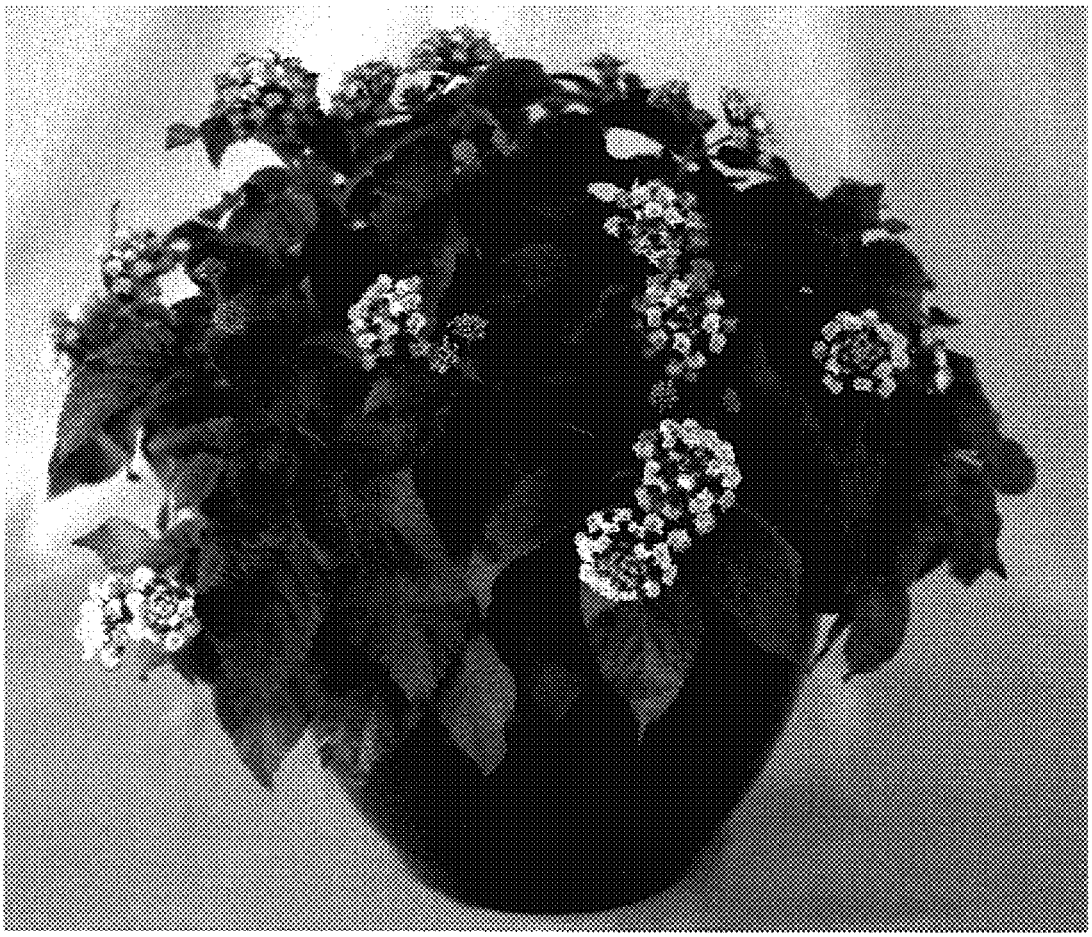

* * * * *